(12) United States Patent
Beyer et al.

(10) Patent No.: US 8,192,505 B2
(45) Date of Patent: Jun. 5, 2012

(54) COSMETIC COMPOSITION FOR COLORING HAIR COMPRISING A DIRECT HAIR DYE AND A CARRIER SYSTEM COMPRISING LIPID VESICLES

(75) Inventors: Monika Beyer, Nidderau-Ostheim (DE); Dirk Teichmüller, Linsengericht (DE)

(73) Assignee: Rovi Cosmetics International GmbH, Schluchtern (DE)

( * ) Notice: Subject to any disclaimer, the term of this patent is extended or adjusted under 35 U.S.C. 154(b) by 0 days.

(21) Appl. No.: 13/156,417

(22) Filed: Jun. 9, 2011

(65) Prior Publication Data

US 2011/0302726 A1    Dec. 15, 2011

(30) Foreign Application Priority Data

Jun. 11, 2010 (DE) .......................... 10 2010 030 001

(51) Int. Cl.
*A61Q 5/10* (2006.01)
(52) U.S. Cl. .............. 8/405; 8/426; 8/455; 8/463; 8/526
(58) Field of Classification Search .............. 8/405, 426, 8/455, 463, 526
See application file for complete search history.

(56) References Cited

U.S. PATENT DOCUMENTS

| 6,183,774 B1 | 2/2001 | Aust et al. | |
|---|---|---|---|
| 7,670,391 B2 * | 3/2010 | Schmenger et al. | ............. 8/405 |
| 2008/0279805 A1 | 11/2008 | Giroud | |

FOREIGN PATENT DOCUMENTS

| DE | 10 2004 028 465 | 6/2004 |
|---|---|---|
| WO | 95/23578 | 9/1995 |

OTHER PUBLICATIONS

German Search Report mailed Feb. 4, 2011 in DE 10 2010 030 001.2 filed Jun. 11, 2010.

* cited by examiner

*Primary Examiner* — Eisa Elhilo
(74) *Attorney, Agent, or Firm* — Drinker Biddle & Reath LLP

(57) ABSTRACT

The present invention concerns cosmetic compositions for coloring hair comprising at least one direct hair dye and a carrier system for the at least one direct hair dye, the use of such compositions in cosmetic formulations for coloring hair and processes for the production of the compositions. To provide a possible way with which the permanence of the bond of direct hair dyes to the hair can be improved, with the aim of direct dyes remaining on the hair for as long as possible to deliver the desired hair color in the desired quality for as long as possible, according to the invention there are proposed compositions of the aforementioned kind in which the carrier system includes lipid vesicles having one or more lipid membranes, wherein the at least one direct hair dye is contained in the lipid vesicles and the lipid vesicles have a positive surface charge, wherein the positive surface charge is caused by the lipid vesicles in the lipid membrane or membranes in addition to the lipids from which the vesicles are made up having positively charged alkyl trimonium salts as charge generators.

16 Claims, No Drawings

COSMETIC COMPOSITION FOR COLORING HAIR COMPRISING A DIRECT HAIR DYE AND A CARRIER SYSTEM COMPRISING LIPID VESICLES

This application also claims priority under 35 U.S.C. §119 and/or §365 to German Application No. 10 2010 030 001.2, filed on Jun. 11, 2010, the entire contents of which are incorporated herein by reference.

The present invention concerns cosmetic compositions for coloring hair comprising at least one direct hair dye and a carrier system for said at least one direct hair dye, the use of such compositions in cosmetic formulations for coloring hair and a process for the production of the compositions.

Many people want to have a hair color which is different from their natural one temporarily or permanently and there is a whole series of processes for imparting a different color to hair.

One of those processes involves using direct hair dyes which are attached to or incorporated in the cuticulas of the hair. That semi-permanent or temporary process therefore involves a coloring in which the naturally present pigment of the hair is not altered so that the new color shade is afforded together with the natural hair color. In contrast thereto there are also processes with hair dyes which chemically change the natural hair color by bonding for example chemically to certain amino acids in the hair.

Many direct hair dyes do not by nature adhere to or be incorporated in the cuticulas with the desired permanence and many do not penetrate into the cortex of the hair at all, for example because of their molecule size. Hair coloring agents with such hair dyes therefore often do not lead to coloring with the desired permanence. There is therefore a need for a possible way of prolonging the permanence of attachment or incorporation of direct hair dyes.

Therefore the object of the present invention is to provide a possible way with which the permanence of the bond of direct hair dyes to or in the hair can be improved. The aim is to provide that direct dyes remain on the hair as long as possible in order to afford the desired hair color of the desired quality for as long as possible.

According to the invention that object is attained by compositions comprising at least one direct hair dye and a carrier system for the at least one direct hair dye, wherein the carrier system includes lipid vesicles with one or more lipid membranes, characterised in that the at least one direct hair dye is contained in the lipid vesicles and the lipid vesicles have a positive surface charge, wherein the positive surface charge is caused by the lipid vesicles in the lipid membrane or membranes in addition to the lipids from which the vesicles are made up having positively charged quaternary ammonium compounds as charge generators, wherein said charge generators are selected from alkyl trimonium salts of the formula:

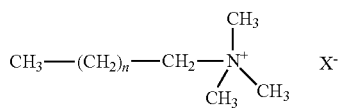

wherein
n is a number of between 18 and 28, and
$X^-$ is an inorganic or organic anion.

By means of the carrier system of the composition according to the invention direct dyes thus provide the desired hair color of the desired quality for longer than without the carrier system of the composition according to the invention, which in fact is to be attributed to the fact that direct dyes by means of the carrier system of the composition according to the invention remain on or in the hair for longer.

Presumably the carrier system of the composition according to the invention provides that the permanence of direct hair dyes being attached to or incorporated in the hair is improved by the dye adhering more firmly to the hair or penetrating better into the hair in order there to be liberated and incorporated in specifically targeted fashion, in which respect however those observations are not intended to be binding in relation to the present invention and the scope of the invention is also not intended to be limited thereby.

In addition the composition according to the invention provides for better stabilisation of the hair dye, which leads to an increase in the amount of intact hair dye which is provided on or in the hair, which in turn has the effect that the desired hair color can be maintained for longer at the desired quality. The positive charge of the vesicle surface is achieved by the lipid vesicles including positively charged molecules as charge generators in addition to the lipids from which the vesicles are made up.

According to the invention the positively charged molecules or charge generators are alkyl trimonium salts (or fatty acid trimonium salts) of the formula:

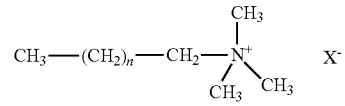

wherein n is an integer of between 18 and 28 and $X^-$ is an inorganic or organic anion.

Preferably $X^-$ is a halogenide ion or the anion of an organic acid selected from a cosmetically compatible carboxylic acid or sulfonic acid. Particularly preferably $X^-$ is bromide, chloride, fluoride, iodide, saccharinate, tosylate or methosulfate.

Preferably n in the above-specified alkyl trimonium salt formula is equal to 22. Particularly preferably the alkyl trimonium salt is behentrimonium chloride.

Preferably the positively charged charge generators are used in an amount of between 0.01 and 10% by weight, preferably between 0.01 and 2.0% by weight, with respect to the total composition.

Preferably the lipid vesicles have a zeta potential in the range of between 1 and 200 mV. The term 'zeta potential' describes the electrical potential of a slipping layer of a moved particle in a suspension. Measurement of the zeta potential can be effected by moving particles through an applied electrical field. The zeta potential can then be calculated from the resulting speed of the particles.

In certain embodiments the lipid vesicles have a zeta potential in the range of between 1 and 150 mV. In many embodiments the vesicles have a zeta potential of between 30 and 100 mV. In particularly preferred lipid vesicles the zeta potential is between 40 and 60 mV.

The particle size of the lipid vesicles according to the invention is preferably between 50 and 1000 nm. In certain embodiment the particle size is in the range of between 100 and 400 nm or in the range of between 100 and 350 nm or in the range of between 100 and 250 nm.

The composition according to the invention can include vesicles with a lipid membrane (nanosomes), two lipid membranes (liposomes) or a plurality of lipid membranes. That permits adaptation to various uses of the composition.

The lipids are preferably selected from ceramides, phospholipids, glycosphingolipids and/or diacylglycosides. They also include sphingomyelins, galactocerebrosides and glucocerebrosides, dihexosides, tri- and tetrahexosides and gangliosides. The phospholipids which can be used in the composition for forming the vesicles can be selected from all cosmetically compatible phospholipids which are capable of forming vesicles (nanosomes or liposomes) in aqueous medium. Preferred phospholipids are lecithin, phosphatidylcholine, phosphatidylethanolamine and phosphatidylserine.

In specific embodiments it is also possible to use mixtures of the above-mentioned lipids. The proportion of lipids with respect to the overall composition is preferably between 1 and 20% by weight or between 1 and 15% by weight or between 4 and 10% by weight.

In the present invention without limitation all water-soluble and fat-soluble hair dyes which are permitted at present and permitted in the future in accordance with the cosmetic regulations as well as any combinations of those dyes which can be encapsulated can be considered as the direct hair dyes. That can involve both lipophilic (oil-soluble) and also hydrophilic (water-soluble) dyes which were isolated from natural sources or produced chemically or biotechnologically, such as for example plant dyes such as henna or indigo, ioanilines, indophenoles, nitrobenzene derivatives, anthraquinone dyes, triphenylmethane dyes, quinone dyes, azo dyes, and cationic and anionic dyes.

Examples of direct hair dyes which can be used in the present invention are without limitation thereto:

TABLE 1 direct hair dyes

| Colipa No. | INCI | CAS No. | EINECS No. | Color Index No |
|---|---|---|---|---|
| B001 | Acid Yellow 1 | | | |
| B005 | Disperse Red 17 | 3179-89-3 | 221-665-5 | CI 11210 |
| B007 | Basic Brown 17 | 68391-32-2 | 269-944-0 | CI 12251 |
| B024 | 4-NITRO-o-PHENYLENEDIAMINE | 99-56-9 | 202-766-3 | CI 76020 |
| B031 | HC RED NO. 13 | 29705-39-3 | 94158-13-1 | |
| B034 | N,N'-BIS(2-HYDROXYETHYL)-2-NITRO-p-PHENYLENEDIAMINE | 84041-77-0 | 281-856-4 | |
| B036 | HC RED NO. 7 | 24905-87-1 | 246-521-9 | |
| B037 | HC BLUE NO. 2 | 33229-34-4 | 251-410-3 | |
| B047 | HC ORANGE NO. 1 | 54381-08-7 | 259-132-4 | |
| B048 | HC RED NO. 1 | 2784-89-6 | 220-494-3 | |
| B051 | 4-AMINO-3-NITROPHENOL | 610-81-1 | 210-236-8 | |
| B052 | 2-HYDROXYETHYLAMINO-5-NITROANISOLE | 66095-81-6 | 266-138-0 | |
| B054 | 3-NITRO-p-HYDROXYETHYLAMINOPHENOL | 65235-31-6 | 265-648-0 | |
| B055 | 2-AMINO-3-NITROPHENOL | 603-85-0 | | |
| B056 | 6-NITRO-o-TOLUIDINE | 570-24-1 | 209-329-3 | |
| B058 | 3-METHYLAMINO-4-NITROPHENOXY-ETHANOL | 59820-63-2 | 261-940-7 | |
| B060 | 2-NITRO-5-GLYCERYL METHYLANILINE | 80062-31-3 | 279-383-3 | |
| B063 | HC YELLOW NO. 11 | 73388-54-2 | — | |
| B066 | HC VIOLET NO. 1 | 82576-75-8 | 417-600-7 | |
| B067 | HC ORANGE NO. 2 | 85765-48-6 | 416-410-1 | |
| B069 | HC YELLOW NO. 9 | 141973-33-3 | 86419-69-4 | |
| B070 | 4-NITROPHENYL AMINOETHYLUREA | 27080-42-8 | 410-700-1 | |
| B071 | HC RED NO. 10 AND HC RED NO. 11 | 95576-89-9 + 95576-92-4 | 408-240-1 | |
| B072 | 2-HYDROXYETHYL PICRAMIC ACID | 99610-72-7 | 412-520-9 | |
| B073 | HC BLUE NO. 12 | 132885-85-9 | 407-020-2 | |
| B075 | HYDROXYETHYL-2-NITRO-P-TOLUIDINE | 100418-33-5 | 408-090-7 (ELINCS) | |
| B077 | HC BLUE NO. 11 | 23920-15-2 | 459-980-7 | |
| B080 | HC YELLOW NO. 7 | 104226-21-3 | | |
| B087 | 4-AMINO-2-NITROPHENYL-AMINE-2'-CARBOXYLIC ACID | 117907-43-4 | — | |
| B089 | 2-CHLORO-6-ETHYLAMINO-4-NITROPHENOL | 131657-78-8 | 411-440-1 | |
| B098 | HC VIOLET NO. 2 | | | |
| B099 | 2-Amino-6-Chloro-4-Nitrophenol | 6358-09-4 | 228-762-1 | |
| B100 | 4-Hydroxypropylamino-3-Nitrophenol | 92952-81-3 | 406-305-9 | |
| B102 | HC YELLOW NO. 13 | 10442-83-8 | | |
| B104 | 1,2,3,4-TETRAHYDRO-6-NITROCHINOXALIN | 158006-54-3 (hydrochloride) | — | |
| B113 | Basic Orange No. 69 | 226940-14-3 | — | CI 112605 |
| B115 | Basic Violet 2 | 3248-91-7 | 221-831-7 | CI 42520 |
| C008 | Basic Red 76 | 68391-30-0 | 269-941-4 | CI 12245 |
| C009 | Basic Brown 16 | 26381-41-9 | 247-640-9 | CI 12250 |
| C010 | Basic Yellow 57 | 68391-31-1 | 269-943-5 | CI 12719 |
| C015 | Orange 4 | 633-96-5 | 211-199-0 | CI 15510 |
| C022 | Red 33 | 3567-66-6 | 222-656-9 | CI 17200 |
| C029 | Yellow 5-Acid Yellow 23 | 1934-21-0 | 217-699-5 | CI 19140 |

TABLE 1-continued direct hair dyes

| Colipa No. | INCI | CAS No. | EINECS No. | Color Index No |
|---|---|---|---|---|
| C040 | Acid Blue 9-Blue 1 | 3844-45-9 | 4223-333-98 | CI 42090 |
| C046 | Basic Blue 7 | 2390-60-5 | | CI 42595 |
| C053 | Acid Red 92 | 18472-87-2 | 242-355-6 | CI 45410 |
| C054 | Yellow 10-Acid Yellow 3 | — | — | CI 47005 |
| C059 | Basic Blue 99 | 68123-13-7 | — | CI 56059 |
| C063 | Acid Violet 43-Ext. Violet 2 | 4430-18-6 | 224-618-7 | CI 60730 |
| C064 | Disperse Violet 1 | 128-95-0 + 116-85-8 | — | |
| C067 | ACID BLUE 62 | 4368-56-3 | 224-460-9 | CI 62045 |
| C117 | HYDROXYANTHRAQUINONEAMINO PROPYLMETHYL MORPHOLINIUM METHOSULFATE | 38866-20-5 | 254-161-9 | |
| C119 | HC RED NO. 8 | 13556-29-1 | 306-778-0 | |
| C129 | HC GREEN NO. 1 | 52136-25-1 | 257-687-7 | |
| C146 | LAWSONE | 83-72-7 | — | CI 75480 |
| C169 | Henna (Lawsonia inermis) | 84988-66-9 | — | |
| C172 | HC BLUE No. 14 | 99788-75-7 | — | |
| C174 | CURRY RED | 25956-17-6 | 247-368-0 | CI 16035 |
| C175 | Acid Red 18 | 2611-82-7 | 220-036-2 | CI 16255 |
| C177 | Acid Red 52 | 3520-42-1 | 222-529-8 | CI 45100 |
| C178 | Acid Green 25 | 4403-90-1 | 224-546-6 | CI 61570 |

Preferably the proportion of direct hair dye in the present invention is between 0.01 and 40% by weight with respect to the overall composition.

In certain embodiments there are combinations of two or more direct hair dyes, wherein the sum of those dyes makes up between 0.01 and 40% by weight with respect to the overall composition.

In an embodiment of the present invention the at least one direct hair dye is contained in the lipid membrane or membranes, that is to say it is bound into the lipid membrane between the lipids of the lipid membrane. Preferably in those embodiments the proportion of hair dye is between 0.01 and 15% by weight with respect to the overall composition. It will be noted however that if the at least one hair dye is a lipophilic hair dye the proportion thereof with respect to the overall composition is preferably between 0.01 and 10% by weight.

In another embodiment the at least one direct hair dye is encapsulated by the lipid membrane or membranes. The term 'encapsulated' is here to be interpreted as meaning that the hair dye is present dissolved in a liquid which is to be found in the vesicle interior formed by the lipid membrane. In a preferred embodiment the hair dye is present dissolved in a water phase enclosed in the vesicle interior. Preferably the proportion of hair dye in those embodiments is between 5 and 40% by weight with respect to the overall composition.

It has been found that direct hair dyes, when present enclosed in the vesicle interior, or when they are contained in the lipid membrane of a vesicle, lead to an improvement in the durability of the hair dyes on the hair surface.

According to the invention the composition is used in cosmetic formulations for coloring the hair. In that case it is possible to add to the composition which contains positively charged lipid vesicles and at least one direct hair dye, further hair dyes which are contained either in the lipid vesicles or outside the lipid vesicles and in the rest of the substance or carrier matrix of the formulation.

The proportion of dyes in the overall formulation is preferably between 0.001 and 40% by weight.

The formulations for coloring hair can contain all adjuvants and additives which are usually employed in cosmetic preparations. In particular the term 'adjuvant' in connection with the present invention includes such additives which act on the physical properties of the vesicle and the stability thereof and/or serve for preservation of the composition. Examples of such adjuvants are oils, alcohols, polyols, antioxidants, gel-forming agents, buffers, preserving agents, bactericides and germ inhibitors, thickeners or complexing agents.

The composition according to the invention can be present in all formulations suitable for coloring hair, for example in the form of a coloring shampoo or coloring styling mousse or in the form of toning lotions, color mousses or toning mousse.

It will be appreciated that all components of the compositions and formulations according to the invention are cosmetically compatible substances. A substance is cosmetically compatible in accordance with this invention if it is non-toxic and can be used in regard to the majority of potential users without the user suffering spontaneously or after a while an unwanted physiological reaction such as for example skin reddening or itching.

Preferably the compositions according to the invention are produced by a process in which:

a) a lipid is dissolved in a short-chain aliphatic monohydric alcohol, preferably ethanol, a lipid solution being obtained, b) a positively charged alkyl trimonium salt is dissolved in the lipid solution from a), c) at least one lipophilic direct hair dye is introduced into the solution from b), d) the solution from c) is put with stirring into a water phase, an emulsion being obtained, e) the pH-value of the emulsion is adjusted to a physiological pH-value of pH 6 to 7 by the addition of a base, preferably soda lye, and f) optionally the emulsion is homogenised by high-pressure homogenisation at a pressure of up to between 1000 bars and 1500 bars.

In this respect the reference to a short-chain aliphatic monohydric alcohol is to be interpreted as meaning a monohydric alcohol having a chain length of between C1 and C4.

Alternatively compositions according to the invention can be produced by a process in which:

a) a lipid is dissolved in a short-chain aliphatic monohydric alcohol, a lipid solution being obtained, b) a positively charged alkyl trimonium salt is dissolved in the lipid solution from a), c) at least one hydrophilic direct hair dye is introduced into a water phase, d) the solution from b) is put with stirring into the water phase from c), an emulsion being obtained, e) the pH-value of the emulsion is adjusted to a physiological pH-value of pH 6 to 7 by the addition of a base, preferably soda lye, and f) optionally the emulsion is homogenised by high-pressure homogenisation at a pressure of up to between 1000 bars and 1500 bars.

In regard to the compositions according to the invention which contain both a lipophilic and also a hydrophilic hair dye, a combination of the two processes described above is particularly preferred.

For the purposes of the original disclosure it is pointed out that all features as can be seen by a man skilled in the art from the present description and the claims, even if they are described in specific terms only in connection with certain other features, can be combined both individually and also in any combinations with others of the features or groups of features disclosed here insofar as that has not been expressly excluded or chemical, physical-chemical, cosmetic, pharmacological or dermatological aspects make such combinations impossible or meaningless. A comprehensive explicit representation of all conceivable combinations of features is dispensed with here only for the sake of brevity and readability of the description.

It is further pointed out that it is self-evident to the man skilled in the art that the embodiments by way of example hereinafter only serve to set out two possible embodiments of the present invention as examples. The man skilled in the art will therefore readily understand that in addition all other embodiments having the features or combinations of features according to the invention as recited in the claims lie within the scope of the invention. A comprehensive explicit representation of all conceivable embodiments within the claimed invention is dispensed with here only for the sake of brevity and readability of the description.

EMBODIMENT 1 (HAIR DYE IN THE LIPID MEMBRANE)

Embodiment 1 concerns lipid vesicles of the following composition:
10.00% by weight of phospholipids (lecithin)
12.00% by weight of ethanol
4.00% by weight of behentrimonium chloride
1.00% by weight of direct hair dye
Ad 100% of water, demineralised To produce the lipid vesicles in accordance with embodiment 1 the lecithin was completely solubilised in ethanol. Behentrimonium chloride and the dye were incorporated with stirring into that solution and completely dissolved. After a homogenisation procedure that lipid phase was incorporated into water.

The particle size of the cationic lipid vesicles produced with that process was checked by means of photon correlation spectroscopy (PCS, Zetamaster S, Malvern Instruments Ltd, UK), wherein the production process was terminated after reaching a mean particle size of a diameter of between about 100 and 350 nm.

EMBODIMENT 2 (HAIR DYE IN THE VESICLE INTERIOR)

Embodiment 2 concerns lipid vesicles of the following composition:
7.00% by weight of phospholipids (lecithin)
12.00% by weight of ethanol
3.00% by weight of behentrimonium chloride
5.00% by weight of direct hair dye
Ad 100% by weight of water, demineralised.

To produce the lipid vesicles in accordance with embodiment 2 the lecithin was completely solubilised in ethanol. Behentrimonium chloride and the dye were successively incorporated with stirring into that solution. Finally the specified amount of water was homogeneously incorporated into that lipid phase and mixed with the lipid phase. That emulsion was then homogenised by means of high-pressure homogenisation).

The particle size of the cationic lipid vesicles produced with that process was checked by means of photon correlation spectroscopy (PCS, Zetamaster S, Malvern Instruments Ltd, UK), wherein the production process was terminated after reaching a mean particle size of a diameter of between about 100 and 400 nm.

The invention claimed is:

1. A cosmetic composition for coloring hair comprising at least one direct hair dye and a carrier system for the at least one direct hair dye, wherein the carrier system includes lipid vesicles with one or more lipid membranes, characterised in that the at least one direct hair dye is contained in the lipid vesicles and the lipid vesicles have a positive surface charge, wherein the positive surface charge is caused by the lipid vesicles in the lipid membrane or membranes in addition to the lipids from which the vesicles are made up having positively charged molecules as charge generators, wherein said charge generators are selected from alkyl trimonium salts of the formula:

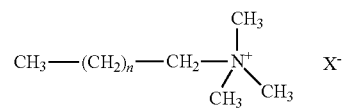

wherein
n is a number of between 18 and 28, and
$X^-$ is an inorganic or organic anion.

2. A composition according to claim 1 wherein $X^-$ is bromide, chloride, fluoride, iodide, saccharinate, tosylate or methosulfate.

3. A composition according to claim 1 wherein the proportion of the charge generators with respect to the overall composition is between 0.01 and 10% by weight.

4. A composition according to claim 1 wherein the zeta potential of the lipid vesicles is between 1 and 200 mV.

5. A composition claim 1 wherein the lipid vesicles are of a particle size of between 50 and 1000 nm.

6. A composition according to claim 1 wherein the lipids from which the vesicles are made up are selected from ceramides, phospholipids, glycosphingolipids and/or diacylglycosides.

7. A composition according to claim 1 wherein the proportion of the lipids with respect to the overall composition is between 1 and 20% by weight.

8. A composition according to claim wherein the at least one direct hair dye is selected from lipophilic and hydrophilic physiologically active substances which were isolated from natural sources or produced chemically or biotechnology or combinations thereof.

9. A composition according to claim 1 wherein the proportion of the at least one direct hair dye with respect to the overall composition is between 0.01 and 40% by weight.

10. A composition according to claim 1 one or more adjuvants.

11. A method of coloring hair comprising applying to the hair a composition according to claim 1.

12. A cosmetic formulation containing a composition according to claim 1.

13. The method according to claim 11 wherein the composition is for topical application.

14. A process for the production of compositions claim 1 wherein
   a) a lipid is dissolved in a short-chain aliphatic monohydric alcohol, a lipid solution being obtained,
   b) a positively charged alkyl trimonium salt is dissolved in the lipid solution from a),
   c) at least one lipophilic direct hair dye is introduced into the solution from b),
   d) the solution from c) is put with stirring into a water phase, an emulsion being obtained,
   e) the pH-value of the emulsion is adjusted to a physiological pH-value of pH 6 to 7 by the addition of a base, and
   f) optionally the emulsion is homogenised by high-pressure homogenisation at a pressure of up to between 1000 bars and 1500 bars.

15. A process for the production of compositions according to claim 1 wherein
   a) a lipid is dissolved in a short-chain aliphatic monohydric alcohol, a lipid solution being obtained,
   b) a positively charged alkyl trimonium salt is dissolved in the lipid solution from a),
   c) at least one hydrophilic direct hair dye is introduced into a water phase,
   d) the solution from b) is put with stirring into the water phase from c), an emulsion being obtained,
   e) the pH-value of the emulsion is adjusted to a physiological pH-value of pH 6 to 7 by the addition of a base, and
   f) optionally the emulsion is homogenised by high-pressure homogenisation at a pressure of up to between 1000 bars and 1500 bars.

16. A formulation according to claim 12 wherein the formulation is for topical application.

* * * * *